(12) United States Patent
Schouwenburg et al.

(10) Patent No.: US 10,842,220 B2
(45) Date of Patent: *Nov. 24, 2020

(54) SYSTEMS AND METHODS FOR GENERATING ORTHOTIC DEVICE MODELS USING SIMULATED PATIENT ANATOMY

(71) Applicant: Aetrex Worldwide, Inc., Teaneck, NJ (US)

(72) Inventors: Kegan L. Schouwenburg, New York, NY (US); Stephen van Beek Faletti, Brooklyn, NY (US); Richard G. Ranky, Ridgewood, NJ (US); John D'Agostino, Nanuet, NY (US); Jacy Krystal Bulaon, Baldwin, NY (US); Peter Yee, Brooklyn, NY (US); Jeff E. Smith, Brooklyn, NY (US)

(73) Assignee: Aetrex Worldwide, Inc., Teaneck, NJ (US)

( * ) Notice: Subject to any disclaimer, the term of this patent is extended or adjusted under 35 U.S.C. 154(b) by 4 days.

This patent is subject to a terminal disclaimer.

(21) Appl. No.: 16/409,064

(22) Filed: May 10, 2019

(65) Prior Publication Data
US 2019/0261733 A1    Aug. 29, 2019

Related U.S. Application Data

(63) Continuation of application No. 15/424,875, filed on Feb. 5, 2017, now Pat. No. 10,327,502.

(Continued)

(51) Int. Cl.
*G06K 9/00* (2006.01)
*A43B 7/14* (2006.01)
(Continued)

(52) U.S. Cl.
CPC .............. *A43B 7/141* (2013.01); *A43B 7/142* (2013.01); *A43B 7/143* (2013.01); *A43B 7/144* (2013.01);
(Continued)

(58) Field of Classification Search
CPC ... G06T 7/0012; G06T 7/0083; G06T 7/0081; G06T 2207/10116; G06T 2207/30004; G06T 5/40; G06T 7/0085; G06T 2207/30068; G06T 7/60; G06F 19/321; G06K 9/4604; G06K 9/52; G06K 9/6267; G06K 9/66; A61B 5/02007; A61B 5/7264; A61B 5/742
See application file for complete search history.

(56) References Cited

U.S. PATENT DOCUMENTS 8,838,263 B2    9/2014  Sivak et al.
9,449,141 B2    9/2016  Schouwenburg et al.
(Continued)

*Primary Examiner* — Duy M Dang
(74) *Attorney, Agent, or Firm* — Lowenstein Sandler LLP

(57) ABSTRACT

The present disclosure relates to systems and methods for generating orthotic device models using simulated patient anatomy. In one implementation, a method comprises receiving images of a body part of a patient; deriving physical measurements from the images; generating anatomy model data of the body part using the physical measurements; and generating orthotic model data based on the anatomy model data, the orthotic model data being representative of an orthotic device.

20 Claims, 8 Drawing Sheets

Related U.S. Application Data

(60) Provisional application No. 62/292,154, filed on Feb. 5, 2016, provisional application No. 62/292,144, filed on Feb. 5, 2016.

(51) Int. Cl.
*A61F 5/14* (2006.01)
*A61F 5/01* (2006.01)
*A43B 7/24* (2006.01)
*A43B 17/00* (2006.01)
*A43B 17/02* (2006.01)
*A43B 17/14* (2006.01)
*A43D 1/02* (2006.01)

(52) U.S. Cl.
CPC .......... *A43B 7/1425* (2013.01); *A43B 7/1435* (2013.01); *A43B 7/1445* (2013.01); *A43B 7/1485* (2013.01); *A43B 7/24* (2013.01); *A43B 17/006* (2013.01); *A43B 17/02* (2013.01); *A43B 17/14* (2013.01); *A43D 1/02* (2013.01); *A61F 5/0111* (2013.01); *A61F 5/14* (2013.01); *A43D 2200/60* (2013.01); *G06T 2210/41* (2013.01)

(56) References Cited

U.S. PATENT DOCUMENTS

| | | | |
|---|---|---|---|
| 10,327,502 B2* | 6/2019 | Schouwenburg | A61F 5/14 |
| 2004/0133431 A1 | 8/2004 | Udiljak et al. | |
| 2008/0111816 A1 | 5/2008 | Abraham et al. | |
| 2008/0292179 A1 | 11/2008 | Busch | |
| 2011/0001794 A1 | 1/2011 | Bhanti | |
| 2011/0082578 A1 | 4/2011 | Stanhope et al. | |
| 2012/0110595 A1 | 5/2012 | Reitman et al. | |
| 2014/0168212 A1 | 6/2014 | Jones | |
| 2014/0188260 A1 | 7/2014 | Layman et al. | |
| 2014/0276235 A1 | 9/2014 | Raniere | |
| 2015/0081076 A1 | 3/2015 | Fernandes | |
| 2015/0165690 A1 | 6/2015 | Tow | |

* cited by examiner

SYSTEMS AND METHODS FOR GENERATING ORTHOTIC DEVICE MODELS USING SIMULATED PATIENT ANATOMY

CROSS-REFERENCE TO RELATED APPLICATION

This application is a continuation of U.S. Non-Provisional patent application Ser. No. 15/424,875, filed on Feb. 5, 2017, which claims the benefit of priority of U.S. Provisional Patent Application No. 62/292,154, filed on Feb. 5, 2016, and of U.S. Provisional Patent Application No. 62/292,144, filed on Feb. 5, 2016, the disclosures of which are hereby incorporated by reference herein in their entireties.

TECHNICAL FIELD

This disclosure relates to the field of corrective orthotic devices, in particular, to generating models from user-captured data to produce orthotic devices.

BACKGROUND

An orthotic insert is a type of orthotic device that, when inserted into a shoe and applied to a foot, supports the foot by redistributing ground reaction forces while properly aligning foot joints during motion. Orthotic inserts are typically used to treat biomechanical deformities as well as inflammatory conditions (e.g., plantar fasciitis) in patients.

Various methods have been employed to produce orthotic inserts. For example, plaster cast, gait scanning, and laser scanning methods attempt to capture plantar geometry in a weight-bearing position. However, such methods are generally slow in acquiring orthotic data, expensive, and limited in the range of characteristics that they can provide to the resulting orthotic device. In such methods, the resulting orthotic device is customizable insofar as it is designed with a particular ailment in mind, while the treatment is implemented as a one-size-fits-all solution that may be far from optimal for some patients.

Moreover, current methods of orthotic insert production are generally limited to the machining of hard materials (subtractive approaches). This also limits the range of characteristics (flexibility, shock absorption, weight, etc.) of the end product. Shapes of the orthotic inserts tend to be mixed and matched from a database, which may result in orthotic inserts that are unique to a particular lab or production facility but not to a particular patient.

SUMMARY

The following is a simplified summary of the disclosure in order to provide a basic understanding of some aspects of the disclosure. This summary is not an extensive overview of the disclosure. It is intended to neither identify key or critical elements of the disclosure, nor delineate any scope of the particular implementations of the disclosure or any scope of the claims. Its sole purpose is to present some concepts of the disclosure in a simplified form as a prelude to the more detailed description that is presented later.

In one aspect of the present disclosure, a method comprises receiving images of a body part of a patient; deriving physical measurements from the images; generating anatomy model data of the body part using the physical measurements; and generating orthotic model data based on the anatomy model data, the orthotic model data being representative of an orthotic device.

In another aspect of the present disclosure, a method comprises identifying a foot and a fiducial marker within one of the plurality of images; computing a physical dimension of the foot based on a known dimension of the fiducial marker; scaling one or more of the plurality of images based on the computed physical dimension of the foot; and deriving a plurality of physical measurements at least partially from the scaled images.

In another aspect of the present disclosure, a method comprises computing a simulated model comprising a skeletal structure of the foot or key anatomical markers of the foot; modifying the simulated model based on the plurality of physical measurements and patient data to generate anatomy model data; computing an exterior surface of the simulated model based on predicted locations of soft tissue with respect to the skeletal structure or landmark; generating orthotic model data based on the computed exterior surface of the simulated model; and generating orthotic model data based on the computed exterior surface of the simulated model.

In another aspect of the present disclosure, a method for producing a custom device for a patient comprises producing a patient-matched structural member, wherein the patient-matched structural member is shaped to fit a portion of a foot of the patient; producing an intermediate layer shaped to fit within a shoe of the patient and be disposed between the patient-matched structural member when the custom devices is worn by the patient, the intermediate layer defining a first outer perimeter; producing a padded support shaped to support the patient's toes; coupling the patient-matched structural member to the padded support to form a lower coupled member, the lower coupled member defining a second outer perimeter; and coupling the intermediate layer to the lower coupled member such that the first outer perimeter substantially aligns with the second outer perimeter. In certain implementations, producing the intermediate layer comprises selecting a cutting die based on a shoe size of the shoe of the patient, and die cutting a laminate panel to produce the intermediate layer. In certain implementations, the intermediate layer comprises a foam. In certain implementations, the patient-matched structural member comprises nylon. In certain implementations, the patient-matched structural member corresponds to an orthotic device produced according to any of the methods described herein.

In one or more of the disclosed implementations, computing devices for performing the operations of the above described implementations are also disclosed. Additionally, in implementations of the disclosure, a computer-readable storage medium stores methods for performing the operations of the above described implementations.

BRIEF DESCRIPTION OF THE DRAWINGS

The present disclosure is illustrated by way of example, and not by way of limitation, in the figures of the accompanying drawings, in which.

DETAILED DESCRIPTION

Figure 1A:
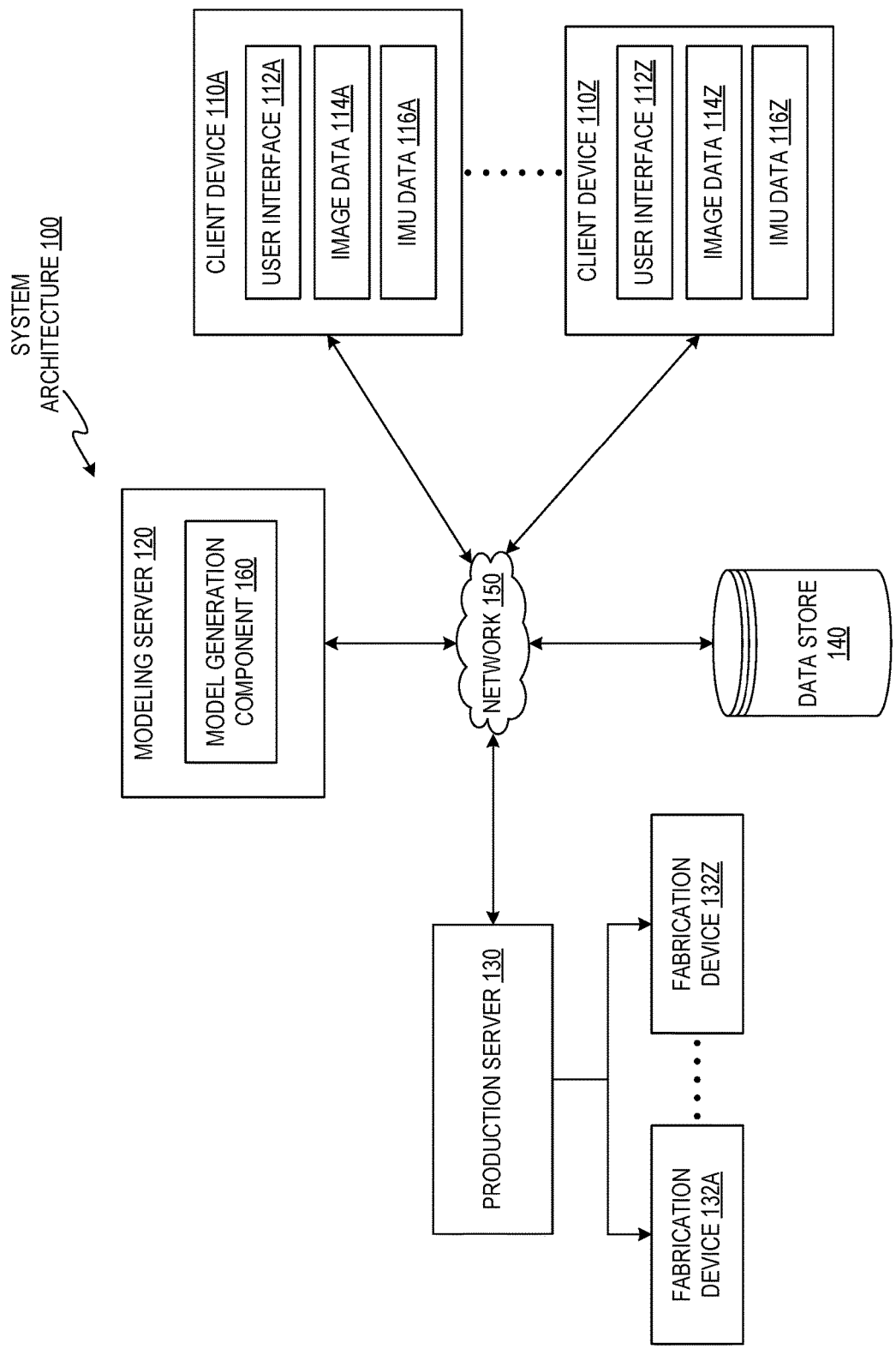
FIG. 1A illustrates an example system architecture in accordance with an implementation of the disclosure.

Implementations are described for producing orthotic devices from user-captured data. Image data of a body part of a patient (e.g., the patient's foot) can be captured using a client device, such as a mobile device having a camera. An interface implemented on the client device can instruct a user of the device (e.g., the patient, a physician, an assistant, etc.) to capture image data (e.g., images and/or video) of the body part. For example, the interface may utilize various indicators (e.g., visual cues) to guide data capture. If the device includes an inertial measurement unit (IMU), then IMU data may also be captured during the image data capture, which may facilitate downstream data processing. The device can also allow for data entry of patient information, which can include physical parameters related to the patient (e.g., height, weight, body mass index, age, pre-existing medical conditions, wear patterns on the patient's shoes, etc.).

The captured image data, IMU data, and patient information may be transmitted to a server, which may derive physical measurements of the patient's anatomy based from the captured image data. The physical measurements and patient information may be used to simulate patient anatomy, which is in turn used to generate orthotic model data (e.g., CAD data) for an orthotic device (e.g., an orthotic shoe insert). In some implementations, the orthotic model data may be generated from a parametric model for which the physical measurements and the patient information serve as inputs. The orthotic model data may be transmitted, for example, to a manufacturing facility that can fabricate an orthotic device from the orthotic model data (e.g. via 3D printing).

The implementations of the present disclosure provide several advantages over traditional orthotic device technologies, and orthotic insert technologies in particular. The implementations described herein leverage the portability, low weight, and accuracy of a mobile device, allowing for a patient to perform his/her own image capture without requiring trained medical personnel. The level of accuracy and consistency in patient anatomy modeling outperforms plaster cast and gait scanning methods. Moreover, the implementations described herein can produce an orthotic insert with variable density by incorporating surface and sub-surface structures that further customize the mechanical properties of the orthotic insert, resulting in an orthotic insert that is extremely thin, cushioned, and patient-optimized all at once.

The term "orthotic device", as used herein, refers to any device worn by or externally applied to an individual that provides neuromuscular support to the individual, provides skeletal support to the individual, and/or provides prophylactic functionality. The term "corrective device", as used herein, refers to a type of orthotic device that provides a therapeutic benefit to an individual (e.g., who may be referred to herein as "a patient") when worn by or externally applied by to the individual. While the implementations herein are described with respect to orthotic devices for treating or supporting a patient's foot (i.e., orthotic shoe inserts), it is to be understood that the systems and methods described herein are applicable to the production of other types of devices. For example, the implementations described herein are generally applicable to the production of devices that are customized to fit to the human body, devices utilizing customization and optimization related to physical human activity, bio-mechanics, and anatomy, processes that can be applied to consumer devices with or without specialized hardware or skill, and devices that utilize components or structures that would be difficult to produce in mass quantities with traditional manufacturing approaches. Such devices may include, but are not limited to, helmets, body armor, sports equipment, prosthetics, casts, splints, clothing, furniture, vehicle seats, vehicle or robotic control mechanisms, physical therapy devices, gloves, surgical instruments, and sterile medical packing.

FIG. 1A illustrates an example system architecture 100, in accordance with an implementation of the disclosure, for generating an orthotic device. The system architecture 100 includes client devices 110A-110Z, a modeling server 120, a production server 130, fabrication devices 132A-132Z, a data store 140, and a network 150 through which the various devices may communicate.

In one implementation, the client devices 110A-110Z may include computing devices such as personal computers (PCs), laptops, mobile phones, smart phones, tablet computers, netbook computers etc. Client devices 110A-110Z may also be referred to as "user devices". An individual user may be associated with (e.g., own and/or use) one or more client devices (e.g., one or more of client devices 110A-110Z). Client devices 110A-110Z may each be owned and utilized by different users at different locations. As used herein, a "user" may refer generally to an individual operator of one or more of client devices 110A-110Z, and may be a patient for which an orthotic device is to be produced, a clinician or physician who may be involved in the preparation of the orthotic device in conjunction with, or on behalf of, the patient, an assistant to the patient, etc.

The client devices 110A-110Z may each implement user interfaces 112A-112Z, respectively. Each of user interfaces 112A-112Z may allow a user of the respective client device 110A-110Z to send and receive information to one or more of the modeling server 120 and the production server 130. For example, one or more of the user interfaces 112A-112Z may be a web browser interface that can access, retrieve, present, and/or navigate content (e.g., web pages such as Hyper Text Markup Language (HTML) pages) provided by the modeling server 120. In one implementation, one or more of the user interfaces 112A-112Z may be a standalone application (e.g., a mobile app), which may have been provided by the modeling server 120 (e.g., as a downloadable application), that allows a user of a respective client device 110A-110Z to send and receive information to the modeling server 120. In one implementation, the user interfaces 112A-112Z guide their respective users in capturing image data of a body part, which is utilized downstream by the modeling server 120 to generate a 3D model of the body part. The term "image data" is intended to include any type of visual data that can be captured by an optical instrument (e.g., a photographic camera, a charge-coupled device (CCD) camera, an infrared camera, etc.), including videos, static images, and video frames.

In one implementation, one or more of the client devices 110A-110Z may capture and store image data 114A-114Z, respectively, which may include one or more static images, videos, and/or audio data (e.g., which may be embedded within the video data or may be a separate audio track). The image data 114A-114Z may be made accessible to other devices of the system architecture 100 via the network 150. For example, captured image data may be transmitted to (e.g., streamed in real-time during capture or transmitted at a later time after capturing the data) the modeling server 120 and/or the data store 140. Each of client devices 110A-110Z may also capture IMU data 116A-116Z, respectively, which may include gyroscopic data, magnetometer data, GPS data, etc., captured by the respective client device while in use. For example, IMU data 116A, which may be captured while a user is operating the client device 110A to capture image data 114A of his/her foot, may be used to estimate the orientation of the client device 110A (e.g., if the client device is a mobile device with a camera). The IMU data 116A may later be leveraged to identify frames of video that best capture the foot to facilitate downstream data processing. For example, the IMU data may be used to determine if the client device 110A is oriented in a manner with respect to the ground (e.g., "level") to ensure that image data 114A of the patient's foot is optimally captured. The IMU data 116A-116Z may be made accessible to other devices of the system architecture 100 via the network 150.

In one implementation, the modeling server 120 may be one or more computing devices (such as a rackmount server, a router computer, a server computer, a personal computer, a mainframe computer, a laptop computer, a tablet computer, a desktop computer, etc.), data stores (e.g., hard disks, memories, databases), networks, software components, and/or hardware components. The modeling server 120 may include a model generation component 160 (which may be executed by a processing device of the modeling server 120) that is capable of: processing and storing patient data, generating three-dimensional (3D) models of a patient's body part (e.g., a patient's foot) based on image data-captured by the patient/user of one of client devices 110A-110Z and/or on patient-related data (e.g., medical data); performing biomechanical simulations of patient anatomy; and generating 3D models of orthotic devices. For example, the model generation component 160 may be capable of generating orthotic model data, including parametric CAD models and hybrid computational/parametric CAD models, and performing manipulations of orthotic model data for orthotic devices (e.g., based on the 3D model of the patient's body part). In some implementations, the model generation component 160 may be implemented on a different device than modeling server 120. For example, in some implementations, one or more of client devices 110A-110Z may implement the model generation component 160, and modeling server 120 may be omitted from the system architecture 100. In other implementations, the modeling server 120 may be combined with the production server 130 as a single server. In one implementation, the modeling server 120 may utilize high performance computing resources (e.g., available via the Internet) by outsourcing data processing functions to high-performance computing devices.

In one implementation, the production server 130 may be one or more computing devices (such as a rackmount server, a router computer, a server computer, a personal computer, a mainframe computer, a laptop computer, a tablet computer, a desktop computer, etc.), data stores (e.g., hard disks, memories, databases), networks, software components, and/or hardware components. The production server 130 may receive orthotic model data from the modeling server 120 via the network 150. The orthotic model data may be converted, by the production server 130, into a format suitable for a particular fabrication process prior to transmitting the data to one or more of the fabrication devices 132A-132Z.

In one implementation, the fabrication devices 132A-132Z are communicatively coupled to the production server 130, as illustrated. In some implementations, one or more of the fabrication devices 132A-132Z may be coupled to one or more of the devices of the system architecture 100 in addition to the production server 130, which may be communicatively coupled to these devices via the network 150. Each of the fabrication devices 132A-132Z may be capable of one or more of injection molding, milling, fused deposition modeling, stereolithography, selective laser sintering, various other types of 3D printing technology, and various other fabrication methods as would be understood by one of ordinary skill in the art.

In one implementation, the data store 140 may be a memory (e.g., random access memory), a cache, a drive (e.g., a hard drive), a flash drive, a database system, or another type of component or device capable of storing data. The data store 140 may also include multiple storage components (e.g., multiple drives or multiple databases) that may also span multiple computing devices (e.g., multiple server computers), and may be cloud-based. In some implementations, the data store 140 may be a part of the modeling server 120. In some implementations, the data store 140 may be distributed among and accessible to one or more of the client devices 110A-110Z, the modeling server 120, and the production server 130. One or more of the devices of the system architecture 100 may utilize the data store 140 to store public and private data, and the data store 140 may be configured to provide secure storage for private data (e.g., patient-specific information).

In one implementation, the network 150 may include a public network (e.g., the Internet), a private network (e.g., a local area network (LAN) or wide area network (WAN)), a wired network (e.g., Ethernet network), a wireless network (e.g., an 802.11 network or a Wi-Fi network), a cellular network (e.g., a Long Term Evolution (LTE) network), routers, hubs, switches, server computers, or a combination thereof. In some implementations, the network 150 may be a combination of different types of networks. Image data 114A-114Z and IMU data 116A-116Z of any of client devices 110A-110Z may be transmitted to modeling server 120 and/or production server 130 via the network 150. Likewise, 3D model data (e.g., of a patient's anatomy) and orthotic model data may be transmitted from the modeling server 120 to any one of the client devices 110A-110Z and the production server 130 via the network 150.

Figure 1B:
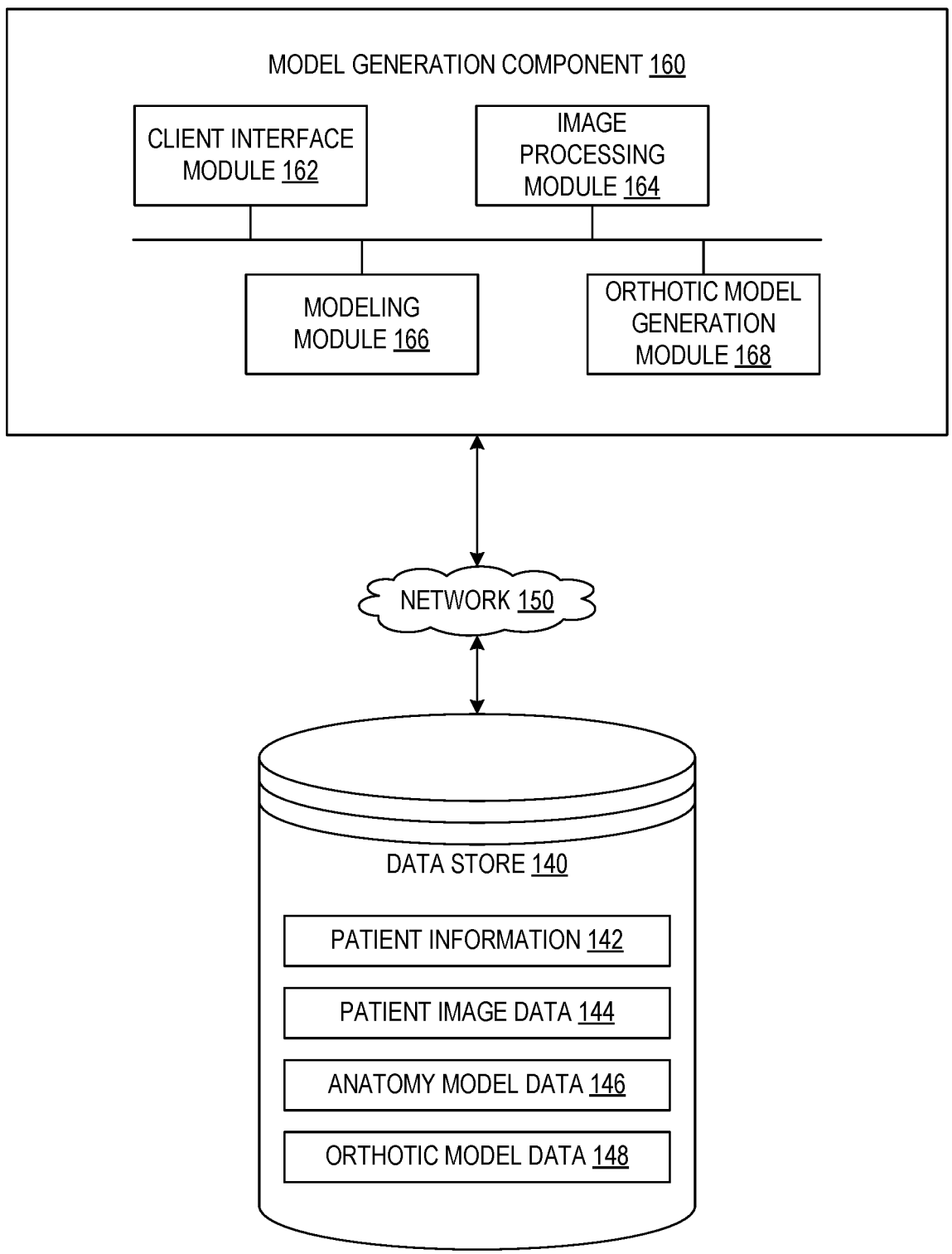
FIG. 1B is a block diagram illustrating features of a model generation component in accordance with an implementation of the disclosure.

FIG. 1B is a block diagram illustrating features of a model generation component 160 in accordance with an implementation of the disclosure. The model generation component 160 may be the same as its identically named counterpart of FIG. 1A. In one implementation, the model generation component 160 includes a client interface module 162, an image processing module 164, a modeling module 166, and an orthotic model generation module 168. More or less components may be included in the model generation component 160 without loss of generality. For example, two or more of the modules may be combined into a single module, or one of the modules may be divided into two or more modules. In one implementation, one or more of the modules may reside on different computing devices (e.g., different server computers, on a client device, distributed among multiple client devices, etc.). The model generation component 160 was described as being implemented by the modeling server 120 of FIG. 1A, but may be implemented by any of the client devices 110A-110Z and the production server 130. For example, a client device (e.g., client device 110A) may be programmed to perform some or all of the functions of the model generation component 160. When the model generation component 160 is implemented on a client device, any functions described with respect to the model generation component 160 that "receive", "transmit", "generate", "retrieve", "identify", "determine", "select", etc., are understood to refer to functions performed by sub-systems or sub-modules within the client device rather than across a network (e.g., the network 150), as would be appreciated by one of ordinary skill in the art.

In one implementation, the model generation component 160 is communicatively coupled to the data store 140. For example, the model generation component 160 may be coupled to the data store 140 via a network (e.g., via network 150). As described with respect to FIG. 1A, the data store 140 may be a memory (e.g., a random access memory), a cache, a drive (e.g., a hard drive), a flash drive, a database system, or another type of component or device capable of storing data. The data store 106 may also include multiple storage components (e.g., multiple drives or multiple databases) that may also span multiple computing devices (e.g., multiple server computers), and may be cloud-based. In one implementation, the data store 140 may include patient information 142, patient image data 144, anatomy model data 146, and orthotic model data 148. While data store 140 is illustrated and described with respect to a single patient, and it is to be understood that data store 140 may store data associated with multiple patients, and the implementations described herein may be performed for multiple patients concurrently.

The term "patient information", as used herein, refers to any alphanumeric data, graphical data, or other type of data that may describe one or more physical aspects of a patient. The patient information 142 may include, but is not limited to, the patient's height, weight, age, a pre-existing medical condition (e.g., a podiatric medical condition), a measured foot length, shoe size, etc. In some implementations, the patient information 142 may include images. For example, the patient may provide images or other form of input indicating the pattern of wear on the underside of his/her shoes or the insides of his/her current insoles. In some implementations, the patient information is provided by the patient (e.g., using one of the client devices 110A-110Z). For example, prior to being prompted to capture image data or after capturing image data, the user may be provided with a user interface, such as a Tillable-form interface, that allows the user to enter physiological and/or medical data associated with the patient (e.g., the user may be the patient, a physician of the patient, or an assistant of the patient or physician). The data may then be transmitted to the modeling server (e.g., modeling server 120) for processing. In some implementations, the patient information may be provided by a physician (e.g., using one of client devices 110A-110Z and/or using modeling server 120). In some implementations, both the patient and the physician may provide portions of the patient information. In some implementations, some or all of the information may have been previously stored in the data store. In some implementations, the patient information may be provided by more than one client device (e.g., provided by more than one of client devices 110A-110Z).

In one implementation, the patient image data 144 includes images and/or video captured by a user of a client device (e.g., one or more of client devices 110A-110Z). The patient image data 144 may also include IMU data stored along with the images and/or video (and may be time-synchronized with video frames), which may be used by the model generation component 160 during image processing. The patient image data 144 may include a plurality of different views of the patient's anatomy. For example, if the patient image data 144 contains images of the patient's foot, such images may include one or more medial images, one or more plantar images, one or more lateral images, one or more anterior images, one or more posterior images, and/or one or more dorsal images.

It is noted that the patient information 142 and the patient image data 144 may collectively include different types of data that may be useful at various stages of the modeling process, namely anatomical data and physiological data. Anatomical data may include data that describes the physical anatomy of the patient in terms of structure of the patient's body. For example, the images of the patient's foot may be representative of the shape and dimensions of the patient's foot, while the patient's weight and body mass index may be representative of the density of the soft tissue of the patient's foot. Physiological data may include data that describes physiological and/or neuromuscular parameters of the patient, such as the patient's age and pre-existing medical conditions. In some implementations, anatomical data may primarily be used to generate models and simulations of patient anatomy, while physiological data may primarily be used to generate orthotic model data.

In one implementation, the model generation component 160 utilizes the client interface module 162 to send/receive information to/from a client device. The client interface module 162 may provide an interface for requesting information from the client device. At the user end, a user interface (e.g., user interface 112A) may be in the form of a web page or a standalone application that may provide an interface to enter patient information, as well as instructions to the user as to how to capture the image data related to a body part of the patient.

Figure 2A:
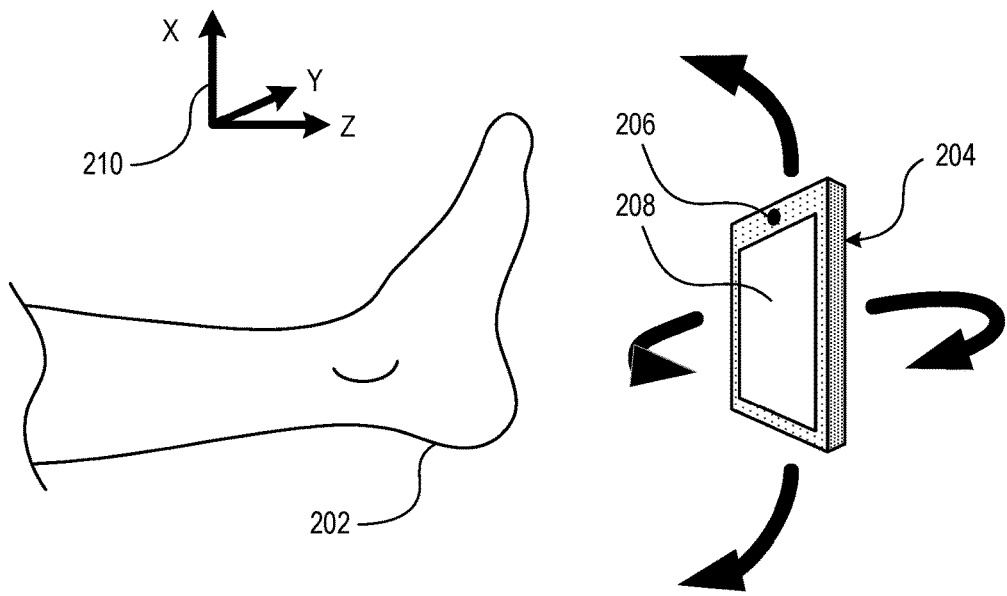
FIG. 2A illustrate the capture of image data according to an implementation of the disclosure.

In one implementation, as illustrated in FIG. 2A, a user may orient a client device 204 (which may correspond to any of client devices 110A-110Z) to capture images and/or video of a foot 202 of the patient based in accordance with instructions/indicators provided on a display 208 of the client device 204 (e.g., a visual cue). In one implementation, the instructions/indicators may alternatively or additionally include audio cues and/or haptic feedback (e.g., a vibration to indicate proper orientation of the client device 204 with respect to the foot 202). A relative coordinate axis 210 may be defined which may serve as a reference point for captured IMU data. As an illustrative implementation, a user captures video of the foot 202 at different orientations with respect to the client device 204 and takes two or more still images of the weight-bearing heel and arch. The video and/or images may be captured using a built-in camera 206 of the client device 204.

Figure 2B:
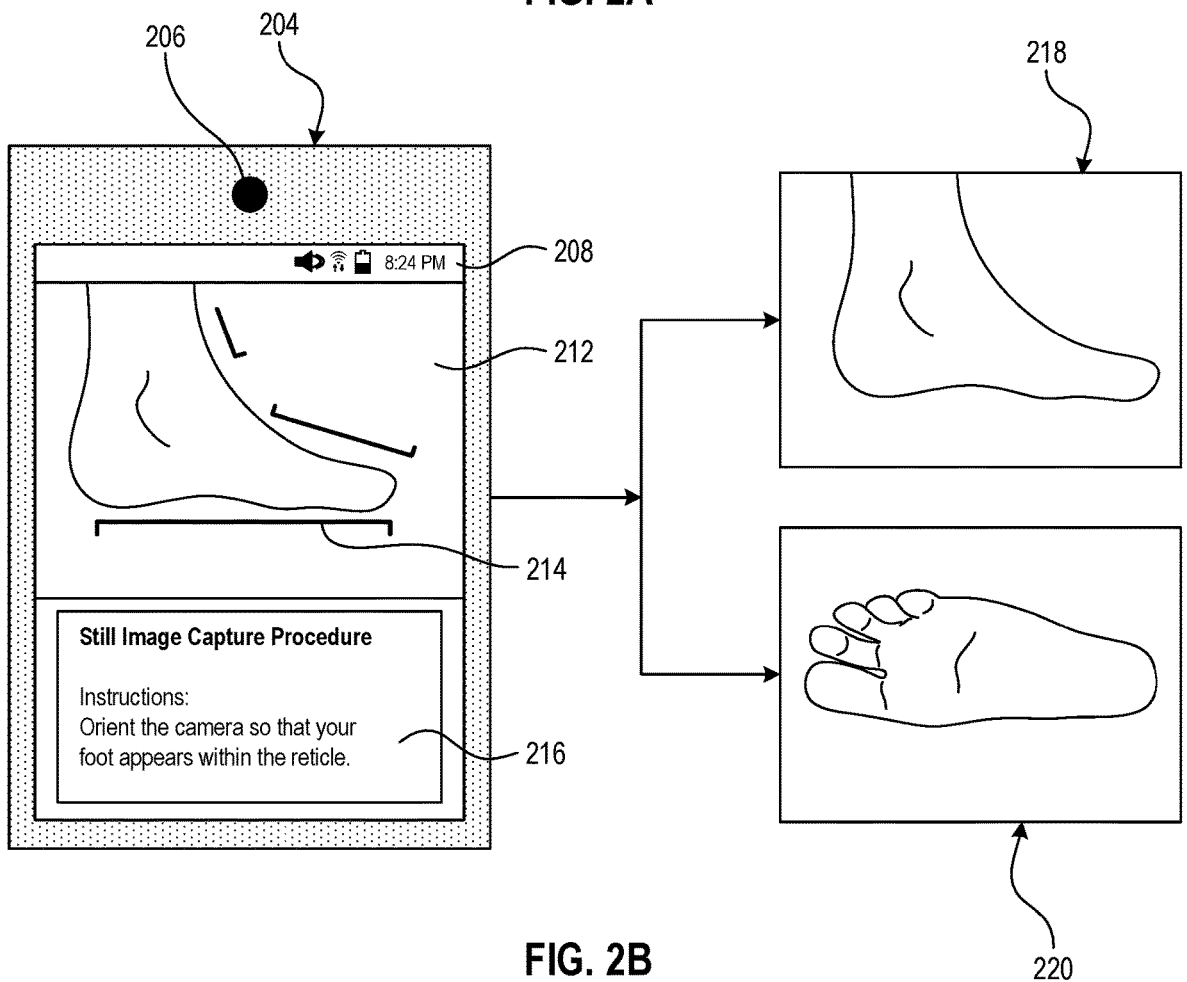
FIG. 2B illustrates the capture of image data according to another implementation of the disclosure.

As illustrated in FIG. 2B, indicators (e.g., visual cues) may be generated for display within an image window 212 within display 208 as the client device 204 is capturing image data of the foot 202. The indicators, such as reticles 214, may serve as indicators for guiding the user to capture relevant regions of the foot in weight-bearing and nonweight-bearing positions. In one implementation, indicators may include overlaid grids, horizontal lines, vertical lines, and foot-shaped targets/overlays. As the user orients the built-in camera 206 and captures image data, the client device 204 may provide additional indicators, such as instructions 216, to inform the user of his/her progress and next steps. In one implementation, visual, audio, and/or haptic cues may indicate successful progress or problems with the capture process. For example, IMU data may be used by the client device 204 to determine that the camera motion has exceeded a threshold translational or angular speed and/or acceleration, and a warning indication may be generated indicating the data captured is potentially unreliable and/or that the data should be recaptured. In some implementations, visual indicators may change shape as video is captured in order to guide the user through particularly helpful views of the foot 202. For example, such visual indicators may include arrows that direct the user. Medial image 218 and plantar image 220 illustrate captured images of the foot.

Referring back to FIG. 1B, in one implementation, the model generation component 160 utilizes the image processing module 164 to identify process the captured images and extract physical measurements therefrom. In some implementations that utilize captured video, individual frames may be selected from the video based on image quality (e.g. focus) and IMU data (if available) in order to best represent the multitude of viewing angles contained in the video. In one implementation, relative position, translational speed, and angular speed of a camera of the client device captured by the IMU of the client device. The data captured by the IMU may be used by the image processing module 164 to determine the uniqueness of information from a given video frame from other video frames based on respective positions/orientations of the other frames, which may be used to save processing time by eliminating video frames that contain redundant data. In addition, the speed of the client device may serve as an indicator of when motion artifacts (e.g., motion blur from rolling shutter cameras) are likely to be present, thus allowing frames captured during periods of fast camera movement to be eliminated.

Captured images (e.g., which may include suitable frames extracted from captured video) is then processed by the image processing module 164 to identify relevant physical measurements of the patient's anatomy. The image processing module 164 may derive the measurements from the images using a combination of computer vision and machine learning algorithms in some implementations. Other implementations may optionally include quality-checking through computer-aided human analysis.

Figure 2C:
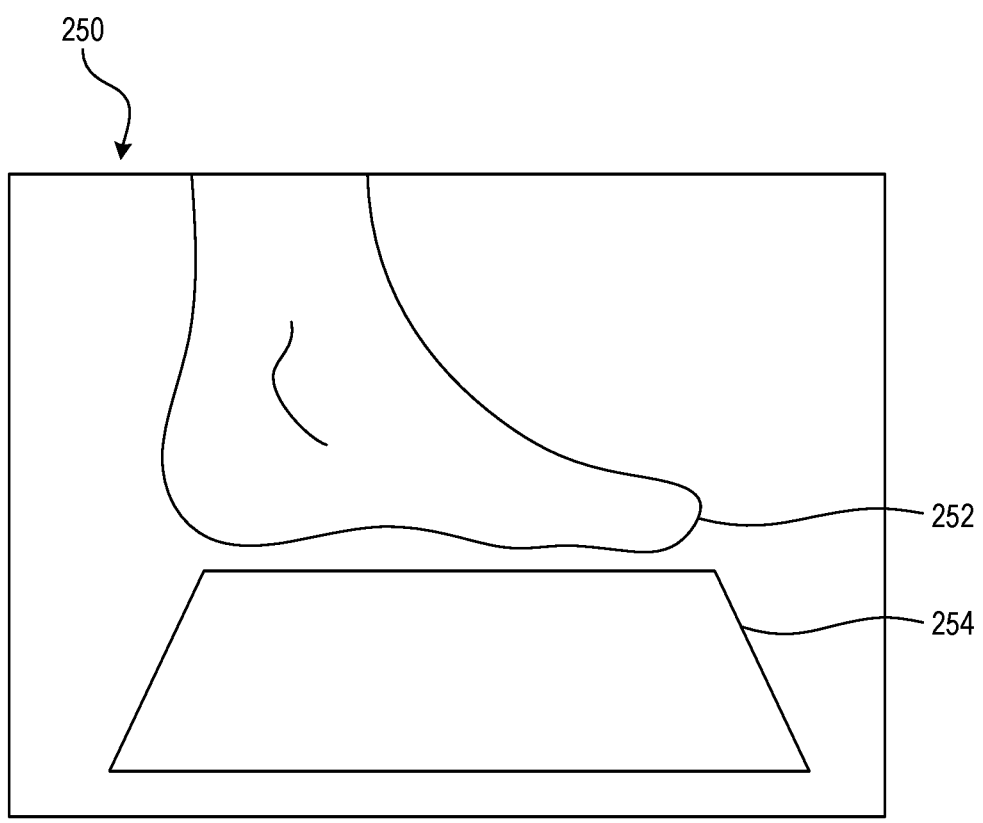
FIG. 2C illustrates a medial image of a foot containing a fiducial marker according to an implementation of the disclosure.

As an example, implementations related to the production of an orthotic shoe insert are now described. One of a plurality of captured images may be used as a scale reference for the foot length. For example, an image of the foot (or body part, generally) in the presence of a fiducial marker (e.g., an object of known size). FIG. 2C illustrates a medial image 250 of a foot 252 containing a sheet of 8.5×11 inch paper 254 as the fiducial marker located near the foot. Scaling of input data is taken with a computer vision and machine learning technique on a patient's foot image and an object of known size such as a sheet of 8.5×11 inch paper. From the medial view, the image processing module 164 may first identify the foot and fiducial marker within the medial image 250, and then identify relevant physical dimensions of each identified object. For example, length and arch height dimensions may be identified for the foot 252, and length and width dimensions may be identified for the paper 254. Using a known dimension of the paper 254 (the 11 inch length), the dimensions of the foot can be extracted. In some implementations, the relative location of the foot and the fiducial marker, as well as the foot view, may be different. For example, the foot may be placed on top of a piece of paper. Other captured images may or may not obtain fiducial markers. In some implementations, one or more of the remaining captured images may be scaled based on an extracted measurement. For example, a plantar image and a medial image may be scaled based on the extracted foot length.

Derived physical measurements may include, but are not limited to, foot length, weight-bearing arch height (e.g., maximum weight-bearing height of the plantar arch at the arch location, weight-bearing subtalar joint angle, total adjusted arch height, arch location (e.g., max plantar arch height location in sagittal and transverse planes in a neutral pose), arch width (e.g., midfoot width, width at peak arch), arch angle, prescription arch height, ball location (e.g., sesamoid location along the sagittal plane), mid heel location (e.g., mid calcaneus location along the sagittal plane), ball width (e.g., maximum forefoot width), and heel width (e.g., maximum plantar calcaneus foot width). The selected images used to perform these derivations may include, but are not limited to, an image of a heel of the foot in the frontal plane, and an image of a medial arch of the foot in the sagittal plane under weight-bearing conditions.

In some implementations, a similar approach may be applied to other body parts for the purposes of extracting physical measurements, including, but not limited to other orthotic devices, prosthetics, and organs. In some implementations, the approach may be applied to inanimate objects (e.g., medical tools) rather than to body parts.

In one implementation, the modeling module 166 may simulate the anatomy of the patient using physical measurements extracted by the image processing module 164 and, optionally, patient information obtained through non-image processing methods (e.g., patient information 142, which may have been entered manually). The modeling module 166 may simulate a digital skeletal structure of the patient anatomy, which may be a biomechanical simulation having rules that govern the mechanical interactions between bones, load-bearing effects, and muscular and soft tissue locations and effects. The simulation may be manipulated (e.g., warped, translated, rotated, skewed, etc.) based on the patient's measurements and information in order to mimic the characteristics of the patient's anatomy. For example, for foot anatomy, a navicular bone of the skeletal structure may be translated along a vertical axis to simulate the patient's measured arch height. In certain implementations, the modeling module 166 may identify key anatomical markers from the captured images and/or measurements, where such markers include, but are not limited to, locations of the metatarsal joints, location and peak of the navicular bone, thickness of surrounding soft tissue, and cross-section of heel anatomy. In some implementations, the modeling module 166 may generate one or more exterior surfaces of the body part, for example, by interpolating the locations of soft tissue (e.g., ligaments, skin) relative to the bone. Patient information, such as age, weight, body mass index (BMI), or preexisting conditions may further influence the simulation of the skeletal structure and/or identification of key anatomical markers to guide the computation of the exterior surfaces. For example, a larger BMI may result in greater displacement between the outer exterior surface and a particular bone than a lower BMI.

In one implementation, the model generation component 160 utilizes the orthotic model generation module 168 to generate orthotic model data for the orthotic device. The orthotic model generation module 168 may use various algorithms to determine optimal shapes and mechanical properties of the orthotic device, which are described by the orthotic model data. The orthotic model data may include information such as, but not limited to, lattice designs and layouts, mesh perforation properties (e.g., hole size/shapes, pitch, etc.), curve locations, variations in lattice density, variable thicknesses, identifying markers (e.g., a Quick Response code) etc. In one implementation, the orthotic model generation module 168 generates a series of surfaces that may be combined to form top, bottom, and interior surfaces of a solid model of the orthotic insert, as described by the orthotic model data. In addition, lattice and mesh structures can be generated to define the shape and density profile of the orthotic insert, which can be placed within target treatment zones (based on the derived measurements and patient information).

In some implementations, the orthotic model data may be representative of an orthotic device, such as a structural member of an orthotic shoe insert. To generate data descriptive of the structural member, the orthotic model generation module 168 may compute its surface topology to match the patient's anatomy (based on the anatomy model data) while allowing for space for an intermediate layer to be placed therebetween. The intermediate layer may correspond to a soft deformable layer capable of deforming during gait while also controlling compression to fit the foot. The orthotic model generation module 168 may account for the type of shoe being worn when computing the surfaces of the structural member and the intermediate layer. The surfaces may be generated according to various curve definitions, including, but not limited to, control points for Bezier and/or non-uniform rational basis spline (NURBS) curves, parameterized tangent definitions, and surface contouring definitions. The geometry of the structural member and intermediate layer may be defined/modified for fitting the anatomy of the patient based on, but not limited to, shoe size, shoe style, patient information (e.g., weight, height, BMI, etc.), and anatomy (e.g., foot length, arch position, etc.). In some implementations, various cut and perforation patterns may be described by the orthotic model data, which may be formed on surfaces of the orthotic device during fabrication.

In some implementations, the orthotic device may be fabricated by a fabrication device based on the orthotic device data. The fabricated orthotic device may form a single, continuous orthotic insert, or may be a single component of multiple components of an orthotic insert. In some implementations, the fabricated orthotic device may be a structural member shaped to fit a portion of the patient's foot. A padded support (which serves as a toe-bed reinforcement region) and an intermediate layer (as described above) may be adhered to each other and/or the structural member to form the completed orthotic insert.

Figure 3:
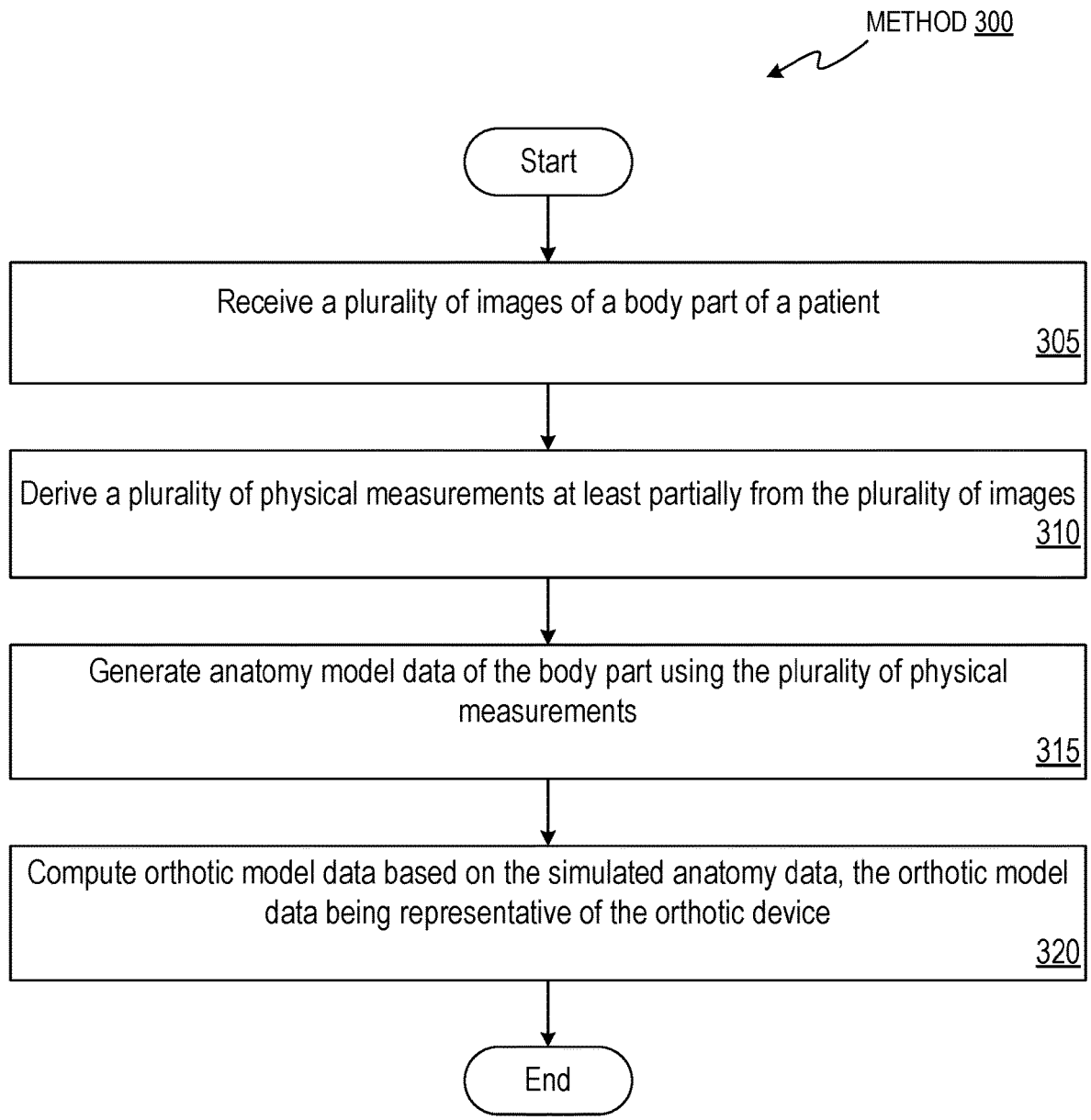
FIG. 3 is a flow diagram illustrating a method for producing an orthotic device according to an implementation of the disclosure.

FIG. 3 is a flow diagram illustrating a method 300 for producing an orthotic device according to an implementation of the disclosure. The method 300 may be performed by processing logic that includes hardware (e.g., circuitry, dedicated logic, programmable logic, microcode, etc.), software (e.g., instructions run on a processing device to perform hardware simulation), or a combination thereof. In one implementation, method 300 may be performed by the model generation component 160 as described with respect to FIGS. 1A and 1B.

Referring to FIG. 3, method 300 begins at block 305 when a processing device (e.g., of modeling server 120) receives a plurality of images of a body part of a patient. The images may be received, for example, from one or more client devices (e.g., one or more of client devices 110A-110Z). In some implementations, additional data may be received by the processing device, including patient information and/or IMU data captured by a client device. In some implementations, the body part is a foot. In other implementations, the plurality of images may be of an inanimate object.

At block 310, the processing device derives a plurality of physical measurements at least partially from plurality of images. At block 315, the processing device generates anatomy model data of the body part using the plurality of physical measurements. At block 320, the processing device computes orthotic model data based on the simulated anatomy data, the orthotic model data being representative of the orthotic device. The orthotic model data may be transmitted to a fabrication device to fabricate the orthotic device based on the orthotic model data. For example, the orthotic device may be fabricated via 3D additive nylon or alternate fabrication processes (e.g., subtractive fabrication, such as 3 or 5 axis milling, or formative such as injection molding) and materials (e.g., a thermoplastic with similar elastic properties to nylon).

Figure 4:
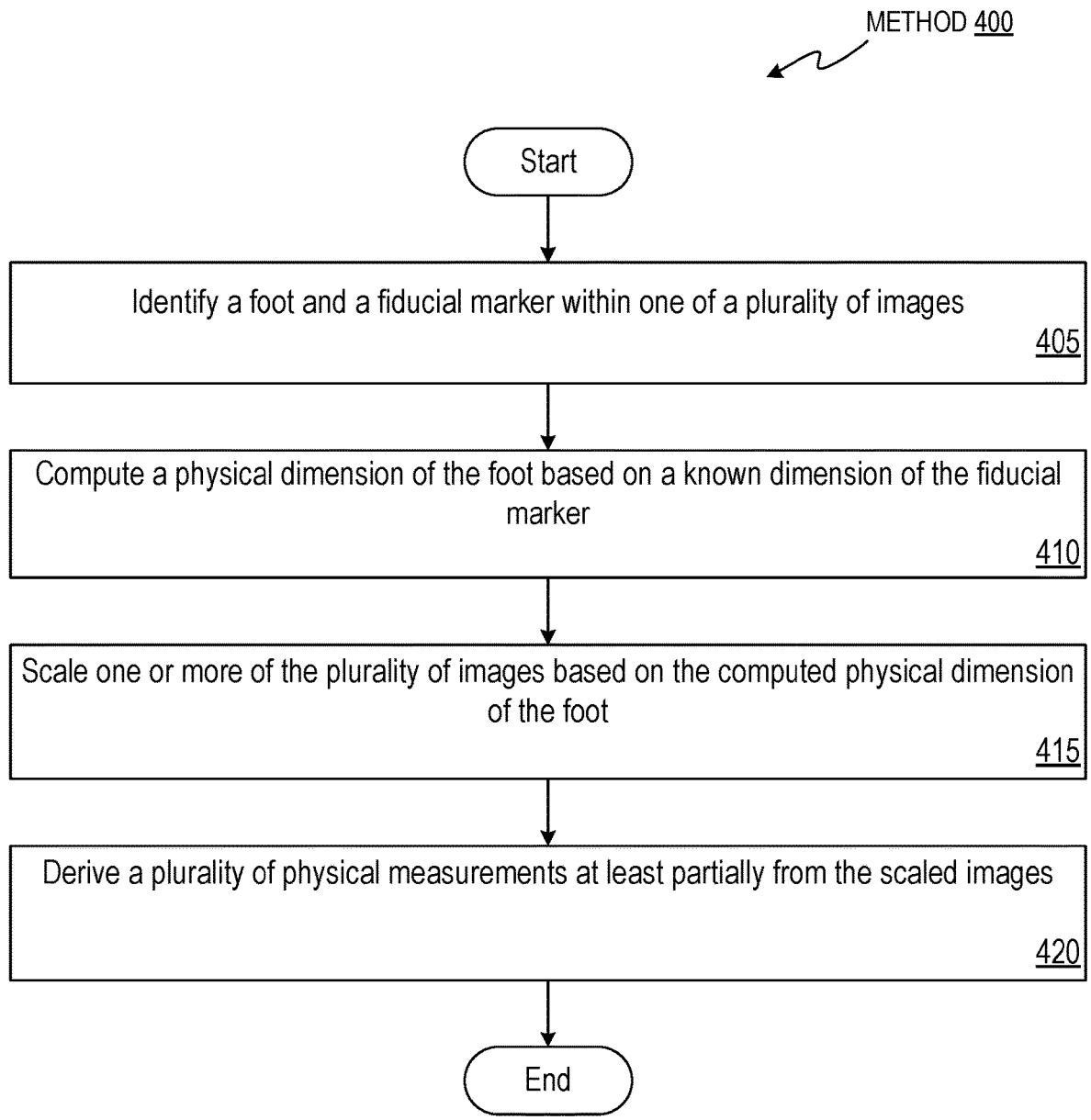
FIG. 4 is a flow diagram illustrating a method for deriving physical measurements from images of a foot.
Figure 5:
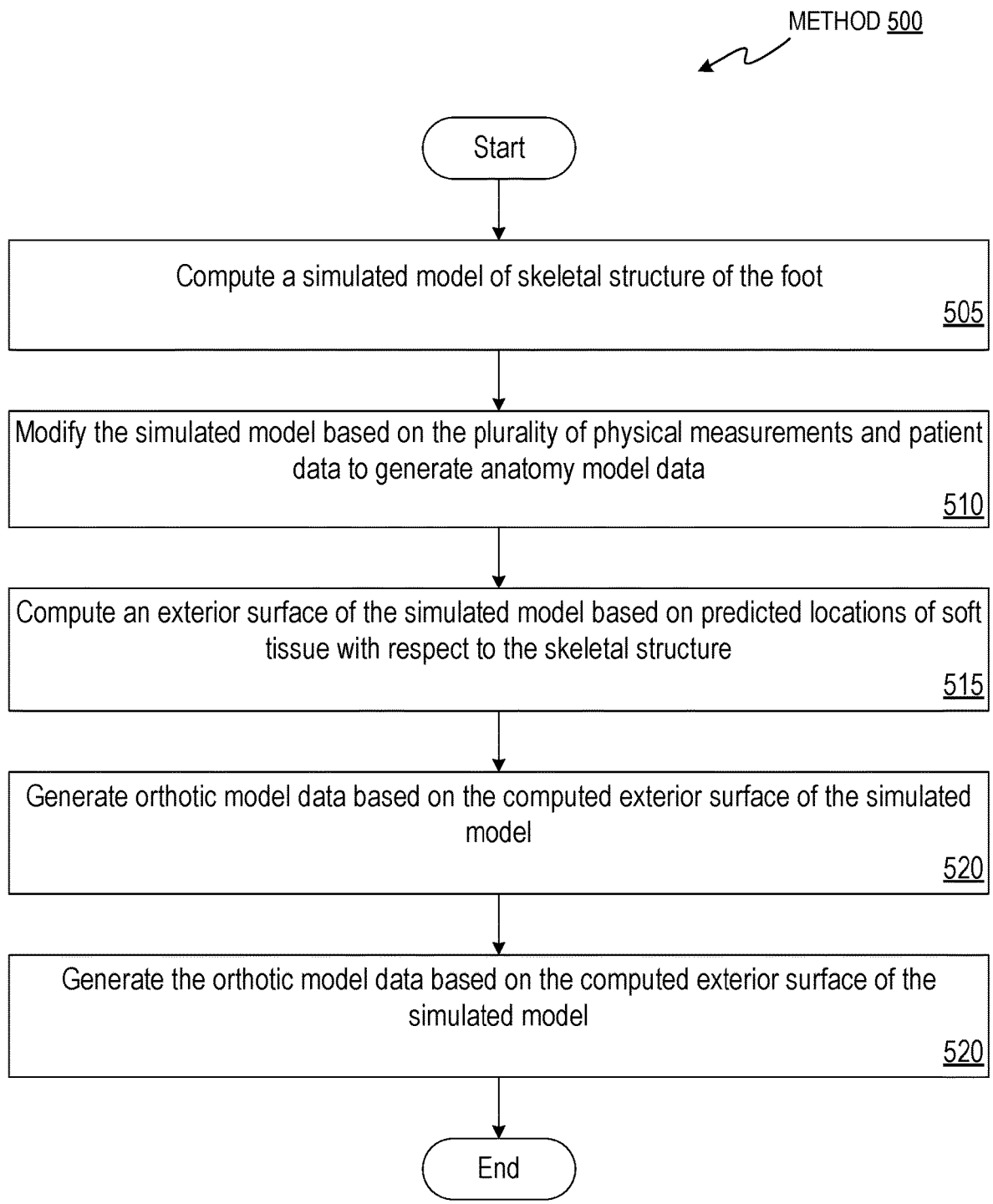
FIG. 5 is a flow diagram illustrating a method for computing orthotic model data for an orthotic insert.

Specific implementations of method 300 for when the patient's body part is a foot (e.g., for the design of an orthotic shoe insert) are now described below with respect to FIGS. 4 and 5. Specifically, FIG. 4 is a flow diagram illustrating a method 400 for deriving physical measurements from images of a foot, and FIG. 5 is a flow diagram illustrating a method 500 for computing orthotic model data for an orthotic insert. Like method 300, methods 400 and 500 may be performed by processing logic that includes hardware (e.g., circuitry, dedicated logic, programmable logic, microcode, etc.), software (e.g., instructions run on a processing device to perform hardware simulation), or a combination thereof. In one implementation, methods 400 and 500 may be performed by the model generation component 160 as described with respect to FIGS. 1A and 1B.

Referring to FIG. 4, method 400 may correspond to block 310 of method 300 when the body part is a foot, with the plurality of images of the foot. For example, in some implementations, the plurality of images includes one or more medial images, one or more plantar images, one or more lateral images, one or more anterior images, one or more posterior images, and/or one or more dorsal images, with any combination of such images, including less than all of each type of image, being contemplated. In some implementations, the plurality of images includes at least one medial image of the foot and/or at least one plantar image of the foot. In some implementations, only a single image of the foot may be used rather than a plurality. In such implementations, the single image may be either a medial image or a plantar image.

Method 400 begins at block 405 when a processing device (e.g., of modeling server 120) identifies, within one of the plurality of images, the foot and a fiducial marker within one of the plurality of images. One or more of the plurality of images may depict the patient's foot in proximity of a fiducial marker (e.g., image 250, which shows the foot 252 and a piece of paper 254).

At block 410, the processing device computes a physical dimension of the foot based on a known dimension of the fiducial marker, for example based on one or more computer vision algorithms (e.g., a segmentation algorithm). In some implementations, the fiducial marker is a piece of paper, a ruler, a coin, or any other object having one or more known dimensions capable of being identified by a computer vision algorithm. The processing device, having identified the foot and the fiducial marker, may identify various dimensions of each such as lengths, widths, and depths. The dimensions may be calibrated based on a known dimension of the fiducial marker. For example, if the fiducial marker is an 8.5×11 inch sheet of paper, the processing device may identify the longest dimension of the fiducial marker, which is a known dimension having a length of 11 inches.

In some implementations, the physical dimension of the foot is a length of the foot. The processing device may directly compute the length of the foot from the known dimension of the fiducial marker. In some implementations, the processing device may compute the length of the foot based on a different dimension of the foot, such as a width. For example, the width may be computed based on the known dimension of the fiducial marker, and the length may then be computed from the width based on an empirical relationship between foot length and foot width.

At block 415, the processing device scales one or more of the plurality of images based on the computed physical dimension of the foot. In some implementations, the medial image and the plantar image are scaled based on the computed length of the foot.

At block 420, the processing device derives a plurality of physical measurements at least partially from the scaled images. In some implementations, the plurality of physical measurements includes an arch length, an arch width, an arch height, a ball length, a ball width, a heel length, a heel width, or a combination thereof (with all possible combinations being contemplated). In other implementations, the plurality of physical measurements includes each of an arch length, an arch width, an arch height, a ball length, a ball width, a heel length, a heel width, and a combination thereof.

Referring to FIG. 5, method 500 begins at block 505 when a processing device (e.g., of modeling server 120) computes a simulated model of skeletal structure of the foot.

At block 510, the processing device modifies the simulated model based on the plurality of physical measurements and patient data to generate the anatomy model data.

At block 515, the processing device warps one or more renderings of the skeletal structure such that the simulated model is representative of the physical measurements of the patient data.

At block 520, the processing device computes an exterior surface of the simulated model based on predicted locations of soft tissue with respect to the skeletal structure. In some implementations, the predicted locations of soft tissue are predicted based on a body mass index of the patient.

At block 525, the processing device generates the orthotic model data based on the computed exterior surface of the simulated model. The orthotic model data is generated to be representative of a portion of the orthotic device that is shaped to match at least part of the computed exterior surface.

For simplicity of explanation, the methods of this disclosure are depicted and described as a series of acts. However, acts in accordance with this disclosure can occur in various orders and/or concurrently, and with other acts not presented and described herein. Furthermore, not all illustrated acts may be required to implement the methods in accordance with the disclosed subject matter. In addition, those skilled in the art will understand and appreciate that the methods could alternatively be represented as a series of interrelated states via a state diagram or events. Additionally, it should be appreciated that the methods disclosed in this specification are capable of being stored on an article of manufacture, such as a computer-readable device or storage media, to facilitate transporting and transferring such methods to computing devices. Accordingly, the term "article of manufacture", as used herein, is intended to include a computer program accessible from any computer-readable device or storage media.

Figure 6:
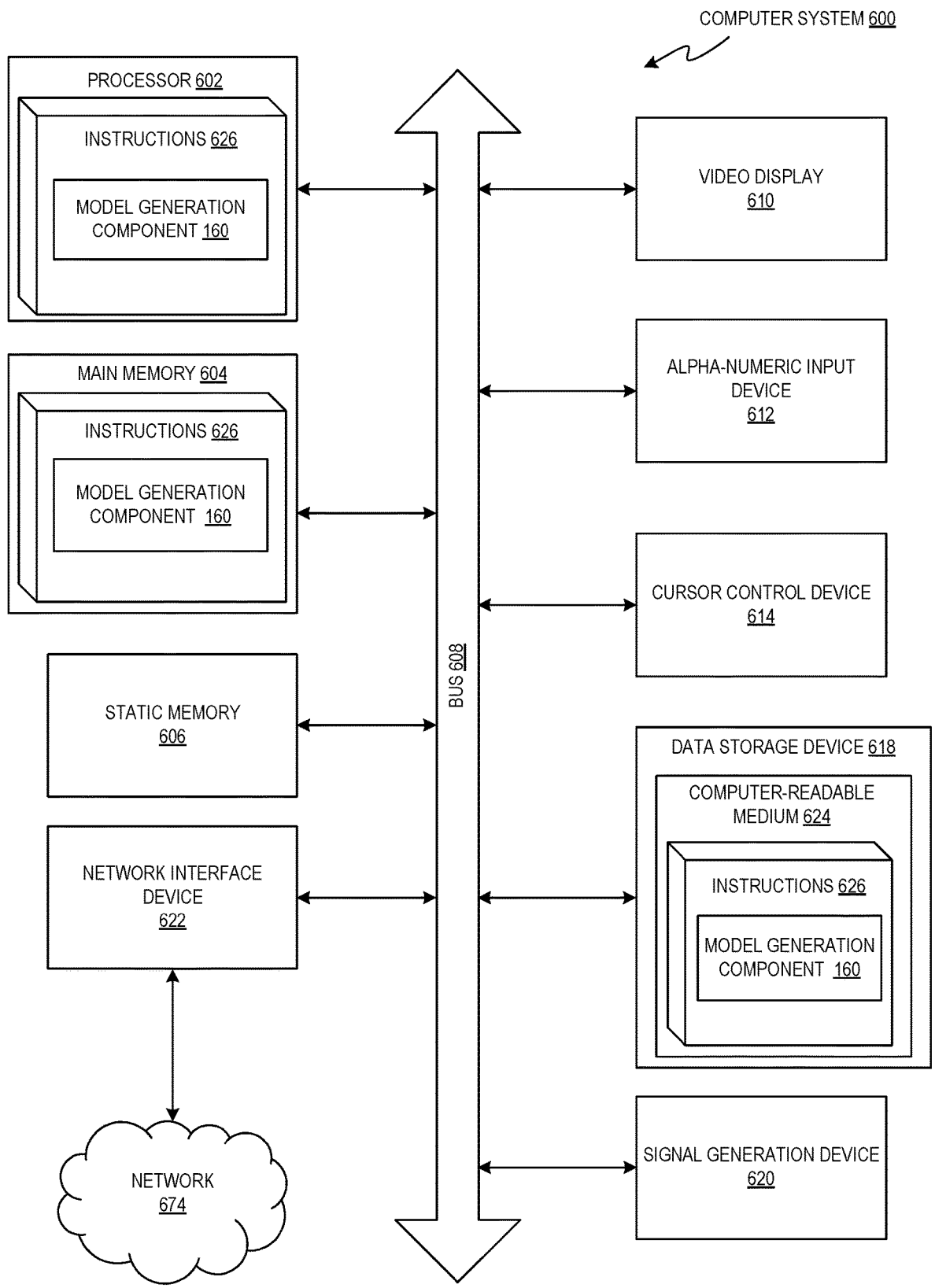
FIG. 6 is a block diagram illustrating an exemplary computer system for use in accordance an implementation of the disclosure

FIG. 6 illustrates a diagrammatic representation of a machine in the exemplary form of a computer system 600 within which a set of instructions, for causing the machine to perform any one or more of the methodologies discussed herein, may be executed. In alternative implementations, the machine may be connected (e.g., networked) to other machines in a LAN, an intranet, an extranet, or the Internet. The machine may operate in the capacity of a server or a client machine in client-server network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein. Some or all of the components of the computer system 600 may be utilized by or illustrative of any of client devices 110A-110Z, modeling server 120, production server 130, fabrication devices 132A-132Z, and data store 140.

The exemplary computer system 600 includes a processing device (processor) 602, a main memory 604 (e.g., read-only memory (ROM), flash memory, dynamic random access memory (DRAM) such as synchronous DRAM (SDRAM) or Rambus DRAM (RDRAM), etc.), a static memory 606 (e.g., flash memory, static random access memory (SRAM), etc.), and a data storage device 618, which communicate with each other via a bus 608.

Processor 602 represents one or more general-purpose processing devices such as a microprocessor, central processing unit, or the like. More particularly, the processor 602 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processor 602 may also be one or more special-purpose processing devices such as an application specific integrated circuit (ASIC), a field programmable gate array (FPGA), a digital signal processor (DSP), network processor, or the like. The processor 602 is configured to execute instructions 626 for performing the operations and steps discussed herein.

The computer system 600 may further include a network interface device 622. The computer system 600 also may include a video display unit 610 (e.g., a liquid crystal display (LCD), a cathode ray tube (CRT), or a touch screen), an alphanumeric input device 612 (e.g., a keyboard), a cursor control device 614 (e.g., a mouse), and a signal generation device 620 (e.g., a speaker). In some implementations, the signal generation device 620 may include a vibrational actuator (e.g., for providing haptic feedback).

The data storage device 618 may include a computer-readable storage medium 624 on which is stored one or more sets of instructions 626 (e.g., software) embodying any one or more of the methodologies or functions described herein. The instructions 626 may also reside, completely or at least partially, within the main memory 604 and/or within the processor 602 during execution thereof by the computer system 600, the main memory 604 and the processor 602 also constituting computer-readable storage media. The instructions 626 may further be transmitted or received over a network 674 (e.g., the network 150) via the network interface device 622.

In one implementation, the instructions 626 include instructions for one or more model generation components 160, which may correspond to the identically-named counterpart described with respect to FIGS. 1A and 1B, and/or a software library containing methods for associating contact identifiers with user accounts. While the computer-readable storage medium 624 is shown in an exemplary implementation to be a single medium, the terms "computer-readable storage medium" or "machine-readable storage medium" should be taken to include a single medium or multiple media (e.g., a centralized or distributed database, and/or associated caches and servers) that store the one or more sets of instructions. The terms "computer-readable storage medium" or "machine-readable storage medium" shall also be taken to include any transitory or non-transitory medium that is capable of storing, encoding or carrying a set of instructions for execution by the machine and that cause the machine to perform any one or more of the methodologies of the present disclosure. The terms "computer-readable storage medium" or "machine-readable storage medium" shall accordingly be taken to include, but not be limited to, solid-state memories, optical media, and magnetic media.

In the foregoing description, numerous details are set forth. It will be apparent, however, to one of ordinary skill in the art having the benefit of this disclosure, that the present disclosure may be practiced without these specific details. In some instances, well-known structures and devices are shown in block diagram form, rather than in detail, in order to avoid obscuring the present disclosure.

Some portions of the detailed description may have been presented in terms of algorithms and symbolic representations of operations on data bits within a computer memory. These algorithmic descriptions and representations are the means used by those skilled in the data processing arts to most effectively convey the substance of their work to others skilled in the art. An algorithm is herein, and generally, conceived to be a self-consistent sequence of steps leading to a desired result. The steps are those requiring physical manipulations of physical quantities. Usually, though not necessarily, these quantities take the form of electrical or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the foregoing discussion, it is appreciated that throughout the description, discussions utilizing terms such as "sending", "receiving", "transmitting", "forwarding", "caching", "causing", "providing", "generating", "adding", "subtracting", "removing", "analyzing", "determining", "enabling", "identifying", "modifying" or the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices.

The disclosure also relates to an apparatus, device, or system for performing the operations herein. This apparatus, device, or system may be specially constructed for the required purposes, or it may include a general purpose computer selectively activated or reconfigured by a computer program stored in the computer. Such a computer program may be stored in a computer- or machine-readable storage medium, such as, but not limited to, any type of disk including floppy disks, optical disks, compact disk read-only memories (CD-ROMs), and magnetic-optical disks, read-only memories (ROMs), random access memories (RAMs), EPROMs, EEPROMs, magnetic or optical cards, or any type of media suitable for storing electronic instructions.

The words "example" or "exemplary" are used herein to mean serving as an example, instance, or illustration. Any aspect or design described herein as "example" or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Reference throughout this specification to "an implementation" or "one implementation" means that a particular feature, structure, or characteristic described in connection with the implementation is included in at least one implementation. Thus, the appearances of the phrase "an implementation" or "one implementation" in various places throughout this specification are not necessarily all referring to the same implementation. Moreover, it is noted that the "A-Z" notation used in reference to certain elements of the drawings is not intended to be limiting to a particular number of elements. Thus, "A-Z" is to be construed as having one or more of the element present in a particular implementation.

It is to be understood that the above description is intended to be illustrative, and not restrictive. Many other implementations will be apparent to those of skill in the art upon reading and understanding the above description. The scope of the disclosure should, therefore, be determined with reference to the appended claims, along with the full scope of equivalents to which such claims are entitled.

What is claimed is:

1. A method of producing an orthotic device, the method comprising:
   receiving, by a processing device, a plurality of images of a body part of a patient;
   deriving, by the processing device, a plurality of physical measurements at least partially from the plurality of images;
   performing, by the processing device, a biomechanical simulation of the body part based at least partially on the plurality of physical measurements to generate anatomy model data; and generating, by the processing device, orthotic model data based on the biomechanical simulation, the orthotic model data being representative of the orthotic device.

2. The method of claim 1, further comprising:
transmitting, by the processing device, the orthotic model data to a fabrication device to fabricate at least a portion of the orthotic device based on the orthotic model data.

3. The method of claim 1, wherein the body part is a foot, and wherein the plurality of images comprises a medial image of the foot and a plantar image of the foot.

4. The method of claim 3, wherein deriving the plurality of physical measurements further comprises:
scaling, by the processing device, the medial image and the plantar image based on a computed physical dimension of the foot; and
deriving, by the processing device, the plurality of physical measurements at least partially from the scaled medial image and the scaled plantar image.

5. The method of claim 1, wherein the body part is a foot, wherein deriving the plurality of physical measurements comprises:
identifying, by the processing device, the foot and a fiducial marker within one of the plurality of images; and
computing, by the processing device, a physical dimension of the foot based on a known dimension of the fiducial marker.

6. The method of claim 5, wherein computing the physical dimension of the foot comprises:
computing, by the processing device, a width of the foot based on the known dimension of the fiducial marker; and
computing, by the processing device, a length of the foot as a function of the width of the foot.

7. The method of claim 1, wherein the body part is a foot, and wherein the plurality of physical measurements comprises an arch length, an arch width, an arch height, a ball length, a ball width, a heel length, and a heel width.

8. The method of claim 1, wherein the body part is a foot, and wherein generating the anatomy model data comprises:
computing, by the processing device, a simulated model comprising a skeletal structure of the foot or key anatomical markers of the foot; and
modifying, by the processing device, the simulated model based on the plurality of physical measurements and patient data to generate the anatomy model data.

9. The method of claim 8, wherein modifying the simulated model comprises:
warping, by the processing device, one or more renderings of the skeletal structure such that the simulated model is representative of the physical measurements of the patient data; and
computing, by the processing device, an exterior surface of the simulated model based on predicted locations of soft tissue with respect to the skeletal structure.

10. The method of claim 9, wherein the predicted locations of soft tissue are predicted based on a body mass index of the patient.

11. The method of claim 10, wherein generating the orthotic model data based on the anatomy model data comprises:
generating, by the processing device, the orthotic model data based on the computed exterior surface of the simulated model, wherein the orthotic model data is generated to be representative of a portion of the orthotic device that is shaped to match at least part of the computed exterior surface.

12. An orthotic device produced according to the method of claim 1.

13. A system for producing an orthotic device, the system comprising:
a memory; and
a processing device operatively coupled to the memory, wherein the processing device is configured to:
receive a plurality of images of a body part of a patient;
derive a plurality of physical measurements at least partially from the plurality of images;
perform a biomechanical simulation of the body part based at least partially on the plurality of physical measurements to generate anatomy model data; and
generate orthotic model data based on the biomechanical simulation, the orthotic model data being representative of the orthotic device.

14. The system of claim 13, wherein the processing device is configured to further:
transmit the orthotic model data to a fabrication device to fabricate at least a portion of the orthotic device based on the orthotic model data.

15. The system of claim 13, wherein the body part is a foot, and wherein the plurality of images comprises a medial image of the foot and a plantar image of the foot, and wherein to derive the plurality of physical measurements, the processing device is further to:
scale the medial image and the plantar image based on a computed physical dimension of the foot; and
derive the plurality of physical measurements at least partially from the scaled medial image and the scaled plantar image.

16. The system of claim 13, wherein the body part is a foot, and wherein to derive the plurality of physical measurements, the processing device is further to:
identify the foot and a fiducial marker within one of the plurality of images; and
compute a physical dimension of the foot based on a known dimension of the fiducial marker.

17. The system of claim 16, wherein to compute the physical dimension of the foot, the processing device is further to:
compute a width of the foot based on the known dimension of the fiducial marker; and
compute a length of the foot as a function of the width of the foot.

18. The system of claim 13, wherein the body part is a foot, and wherein to generate the anatomy model data, the processing device is further to:
compute a simulated model comprising a skeletal structure of the foot or key anatomical markers of the foot;
modify the simulated model based on the plurality of physical measurements and patient data to generate the anatomy model data;
warping one or more renderings of the skeletal structure such that the simulated model is representative of the physical measurements of the patient data; and
compute an exterior surface of the simulated model based on predicted locations of soft tissue with respect to the skeletal structure, wherein the predicted locations of soft tissue are predicted based on a body mass index of the patient.

19. The system of claim 18, wherein to generate the orthotic model data based on the anatomy model data, the processing device is further to:
generate the orthotic model data based on the computed exterior surface of the simulated model, wherein the orthotic model data is generated to be representative of a portion of the orthotic device that is shaped to match at least part of the computed exterior surface.

20. A non-transitory computer-readable medium having instructions encoded thereon that, when executed by a processing device, cause the processing device to:
receive a plurality of images of a body part of a patient;
derive a plurality of physical measurements at least partially from the plurality of images;
perform a biomechanical simulation of the body part based at least partially on the plurality of physical measurements to generate anatomy model data; and
generate orthotic model data based on the biomechanical simulation, the orthotic model data being representative of an orthotic device.

* * * * *